United States Patent [19]
Nishizawa et al.

[11] Patent Number: 5,905,263
[45] Date of Patent: May 18, 1999

[54] DEPTH DOSE MEASURING DEVICE

[75] Inventors: Hiroshi Nishizawa; Kazunori Ikegami; Kunio Madono; Eisaku Teratani; Satoshi Senoo, all of Tokyo, Japan

[73] Assignee: Mitsubishi Denki Kabushiki Kaisha, Tokyo, Japan

[21] Appl. No.: 08/864,462

[22] Filed: May 29, 1997

[30] Foreign Application Priority Data

Nov. 26, 1996 [JP] Japan .................................. 8-315028

[51] Int. Cl.⁶ ............................................ G01T 1/20
[52] U.S. Cl. ...................................... 250/368; 250/367
[58] Field of Search ............................ 250/370.07, 367, 250/368, 369, 336.1, 370.11, 390.11

[56] References Cited

U.S. PATENT DOCUMENTS

| | | | |
|---|---|---|---|
| 3,984,332 | 10/1976 | Nelson et al. | 250/368 |
| 5,155,366 | 10/1992 | Miller | 250/368 |
| 5,266,803 | 11/1993 | Heffelfinger | 250/458.1 |
| 5,281,820 | 1/1994 | Groh et al. | 250/368 |
| 5,352,897 | 10/1994 | Horikawa et al. | 250/370.09 |
| 5,391,879 | 2/1995 | Tran et al. | 250/367 |

FOREIGN PATENT DOCUMENTS

| | | | |
|---|---|---|---|
| 55-128179 | 10/1980 | Japan | 250/364 |
| 57-50672 | 3/1982 | Japan | 250/368 |
| 58-92979 | 6/1983 | Japan | 250/368 |
| 2071456 | 9/1981 | United Kingdom | 250/369 |

OTHER PUBLICATIONS

"A Scintillating Fiber Depth–Dose Measuring Device for Electron Beam Therapy" p. 52, 2a–I–4, 33–th Isotope Research and Representation Cnf. in Science and Engineering.

Catalog of 240 Type CIPS dose plotting system of 3–dimensional computer control, Toyo Medic Corp., Japan.

"Standard Measuring Method of Absorbed Dose for High–Energy X–Ray and Electron Beam in Radiotherapy", Apr. 20, 1989, Ed. Physical Section in Japan Radiological Society, Kabushikikaisya Tusyo Sangyou Kenkyusya, Japan.

Primary Examiner—Edward J. Glick
Assistant Examiner—Darren M. Jiron
Attorney, Agent, or Firm—Sughrue, Mion, Zinn, Macpeak & Seas, PLLC

[57] ABSTRACT

In a depth dose measuring device, a light is outputted from an end surface of a block-type detector (202) formed by tying a plurality of scintillation fibers in a bundle, a spectroscope (204) is used to disperse the light so as to measure an amount of light having a wavelength corresponding to an emission spectrum of the scintillation fibers, a picture measuring device (205) and a picture processing device (206) calculate an emission distribution of only a scintillation light depending upon an emission distribution in which the scintillation light and a Cerenkov light are mixed, and a result is displayed on a display device (207).

8 Claims, 8 Drawing Sheets

DEPTH DOSE MEASURING DEVICE

BACKGROUND OF THE INVENTION

1. Field of the Invention

The present invention relates to a depth dose measuring device to measure a depth dose in the human body, used to determine operating conditions of a cancer curing device using particle beams or corpuscular radiations such as an electron beam, X ray and the like.

2. Description of the Prior Art

Figure 8:
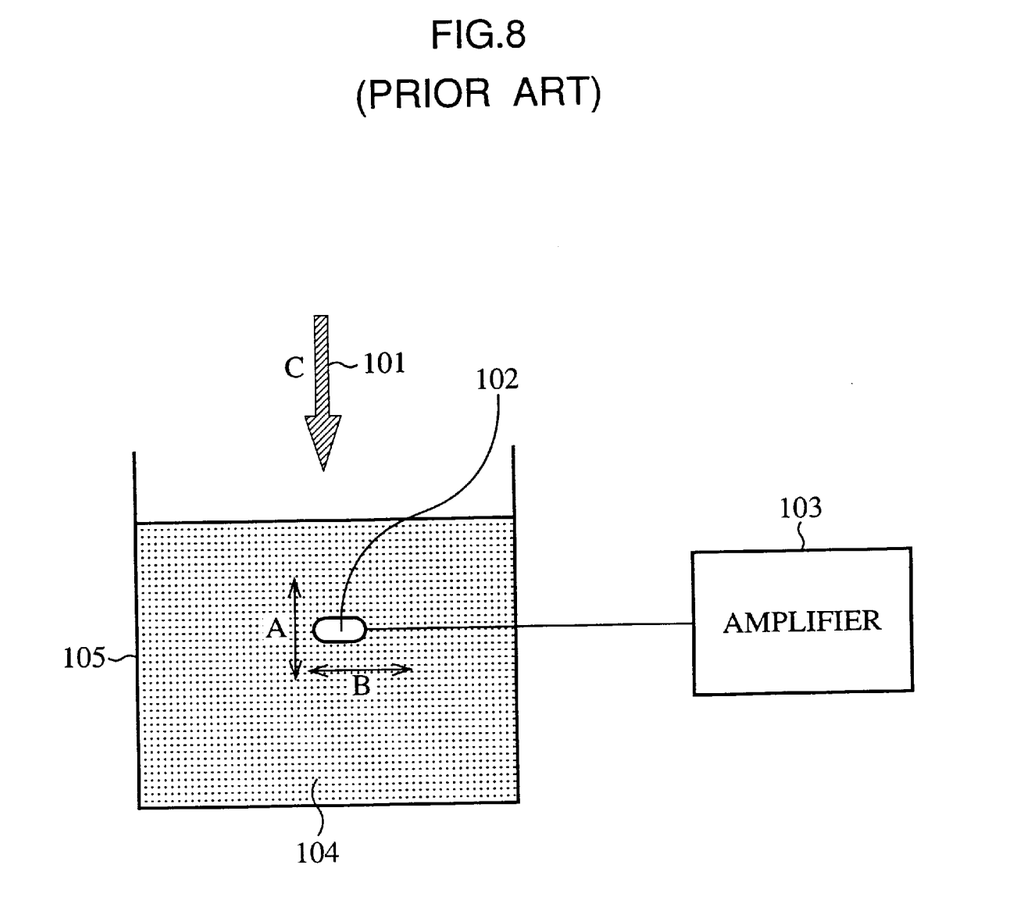
FIG. 8 is a block diagram showing a conventional depth dose measuring device.

FIG. 8 is a diagram showing a conventional method of measuring a depth dose distribution. In the drawing, reference number 104 denotes a water phantom accommodated in a container 105, 102 is an ionization chamber disposed in the water phantom 104, 103 is an amplifier to amplify an absorbed dose signal obtained from the ionization chamber 102, and 101 is a particle beam or a corpuscular beam with which the water phantom 104 is irradiated.

In the conventional depth dose measuring device having the structure shown in FIG. 8, the ionization chamber 102 disposed in the water phantom 104 measures an absorbed dose at a disposed position. The ionization chamber 102 is moved in a depth direction A and in a direction perpendicular to a beam axis C of the particle beam, that is, in a horizontal direction B, thereby measuring the absorbed dose distribution. The amplifier 103 is used to amplify and measure the amount of ionization obtained by the particle beam 101 ionizing air in the ionization chamber 102 disposed in the water phantom 104. In order to measure the absorbed dose distribution, the ionization chamber 102 is moved in the depth direction A and in the horizontal direction B, and the amount of ionization is measured for each movement.

The conventional depth dose measuring device has the above structure. Thus, in order to measure the depth dose distribution, it is necessary to move the ionization chamber 102 in the water phantom 104 for each measurement, resulting in requiring an extremely long time and a lot of labor. Further, three-dimensional dose distribution measurement requires a vast amount of time and labor.

Further, when a variation is caused in the output of a particle beam irradiation device such as an electron beam irradiation device, or X ray irradiation device, the depth dose must be measured from the beginning once again. Thus, the depth dose measurement requires an extremely long time and a lot of labor.

SUMMARY OF THE INVENTION

The present invention is made to overcome the problems of the above conventional depth dose measuring device. It is an object of the present invention to provide a depth dose measuring device in which a depth dose can be measured in a short time, and a distribution of a depth dose can be measured at high accuracy.

According to a preferred embodiment of the present invention, for achieving the above-mentioned object, there is provided a depth dose measuring device comprising detecting means for receiving a particle beam as input, and outputting a light caused by the particle beam from an end surface, light detecting means for detecting the light outputted from the detecting means, and outputting a result of the detection, picture signal processing means for processing the result of the detection outputted from the light detecting means, and a display device for displaying a result of the processing performed in the picture signal processing means. In the depth dose measuring device, the a measurement is made of an amount of light having a wavelength corresponding to a spectrum of the light caused in the detecting means.

Further, in a depth dose measuring device according to the present invention, detecting means comprises a block obtained by tying a plurality of scintillation fibers in a bundle, a light outputted from an end surface of the detecting means is dispersed by a spectroscope, and a measurement is made of an amount of light having a wavelength corresponding to the emission spectrum of the scintillation fibers.

Further, in a depth dose measuring device according to the present invention, a band-pass filter corresponding to a wavelength of emission of scintillation fibers is used to measure an amount of light outputted from an end surface of the detecting means.

Further, in a depth dose measuring device according to the present invention, the detecting means includes a fiber block obtained by alternately disposing a plurality of scintillation fibers and a plurality of regular optical fibers. Only lights obtained from the scintillation fibers are outputted from a first end surface of the detecting means. Only lights obtained from the regular optical fibers are outputted from a second end surface, and a picture measuring device has two measuring systems to calculate a difference between the lights obtained from the first end surface and the lights obtained from the second end surface.

Further, in a depth dose measuring device according to the present invention, a light obtained from a scintillation fiber and a light obtained from a regular optical fiber are outputted from a certain end surface of detecting means, a luminance distribution of both the lights is measured by a picture measuring device serving as picture measuring means such as a camera, and picture processing is performed to calculate a difference between both the lights.

Further, in a depth dose measuring device according to the present invention, a measurement is made of a light outputted from an end surface of block-type detecting means including a plurality of regular optical fibers.

Further, in a depth dose measuring device according to the present invention, clear plastic blocks are disposed at both ends of a block comprising a plurality of short scintillation fibers in order to form detecting means.

Further, in a depth dose measuring device according to the present invention, a clear plastic block forming detecting means is formed to have one side longer than one side of a scintillation fiber block, thereby eliminating an effect of a reflected light generated at the peripheral portion or the end portion of the clear plastic block.

The above and further objects and novel features of the invention will more fully appear from the following detailed description when the same is read in connection with the accompanying drawings. It is to be expressly understood, however, that the drawings are for purpose of illustration only and are not intended as a definition of the limits of the invention.

BRIEF DESCRIPTION OF THE DRAWINGS

These and other objects, features, aspects and advantages of the present invention will become more apparent from the following detailed description of the present invention when taken in conjunction with the accompanying drawings, in which.

DESCRIPTION OF THE PREFERRED EMBODIMENTS

Other features of this invention will become apparent through the following description of preferred embodiments which are given for illustration of the invention and are not intended to be limiting thereof.

Preferred embodiments of the depth dose measuring device according to the present invention will now be described with reference to the drawings.

First embodiment

Figure 1:
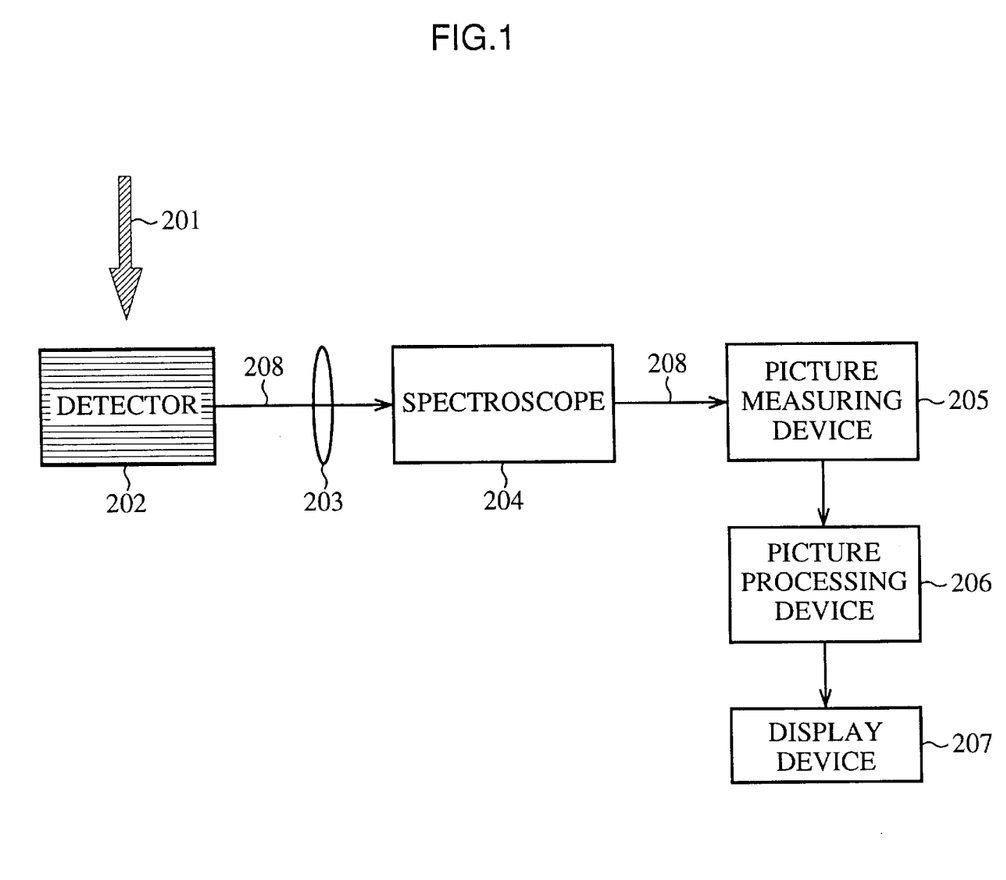
FIG. 1 is a block diagram showing a depth dose measuring device according to the first embodiment of the present invention.

FIG. 1 is a block diagram showing a depth dose measuring device according to the first embodiment of the present invention. In the drawing, reference number 201 designates a particle beam such as electrons, X rays, protons, baryons, and the like, 202 is a detector having a block form obtained by tying scintillation fibers in a bundle, 203 is an optical system such as a lens, or a taper fiber (light guide), 204 is a spectroscope to disperse a light 208 outputted from the detector 202, 205 is a picture measuring device such as CCD camera to measure a light sent from the spectroscope 204, 206 is a picture signal processing device (hereinafter abbreviated as picture processing device) to take as input and process picture signals transmitted from the picture measuring device 205, and 207 is a display device to display a result of the picture processing performed in the picture processing device 206, that is, an absorbed dose distribution.

A description will now be given of the operation of the depth dose measuring device of the first embodiment having the structure shown in FIG. 1.

First, the particle beam 201 is incident on the detector 202, and the incident particle beam 201 emits a light in the detector 202. Next, the detector 202 transmits the internally emitted light to an end surface of the detector 202. Thereafter, the light transmitted to the end surface of the detector 202 passes through the optical system 203, the spectroscope 204, the picture measuring device 205, and the picture processing device 206 in this order. Finally, the display device 207 displays the absorbed dose distribution.

The detector 202 internally emits a scintillation light whose amount is proportional to energy absorbed into the detector 202, and a Cerenkov light according to a speed at which the particle beam 201 passes through the detector 202. In order to accurately measure an amount of absorbed dose, it is necessary to remove the Cerenkov light, thereby measuring only the scintillation light.

The scintillation light emits a light having a wavelength according to a scintillator. On the other hand, a wavelength distribution of the Cerenkov light is inversely proportional to the square of the wavelength, and has a continuous distribution ranging from an ultraviolet region to a blue region.

There may be selected a scintillator emitting a light of a region having a longer wavelength than that of the blue region, for example, a green region, and the scintillator may be used in the detector 202. In this case, since an obtained scintillator light and the Cerenkov light have different wavelengths, the spectroscope 204 can be used to easily discriminate therebetween. As a result, it is possible to accurately measure a depth dose as distribution.

Further, even when the scintillator emits a light having a wavelength of the blue region, a comparison may be made between an amount of light of the scintillator and an amount of Cerenkov light in the vicinity of a scintillator emission wavelength region to subtract the amount of Cerenkov light from the amount of light of the scintillator. It is thereby possible to obtain only the amount of scintillation light. As a result, the depth dose distribution can accurately be measured.

Second embodiment

Figure 2:
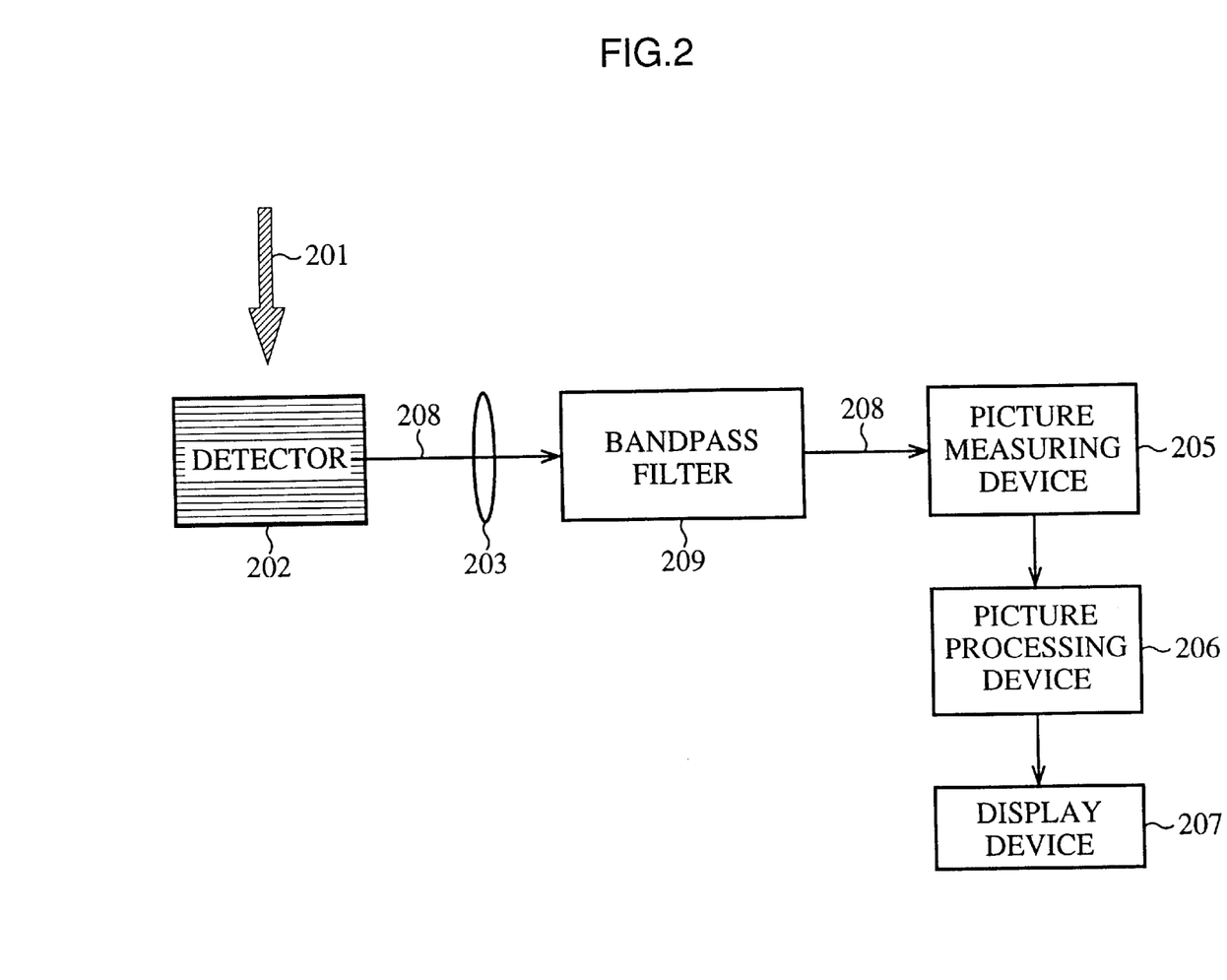
FIG. 2 is a block diagram showing a depth dose measuring device according to the second embodiment of the present invention.

FIG. 2 is a block diagram showing a depth dose measuring device according to the second embodiment of the present invention. In the drawing, the same reference numbers are used for component parts identical with those in the first embodiment shown in FIG. 1, and descriptions thereof are omitted.

The depth dose measuring device according to the second embodiment differs from the depth dose measuring device according to the first embodiment shown in FIG. 1 in that the former has a band-pass filter 209 disposed between an optical system 203 and a picture measuring device 205 instead of the spectroscope 204. The band-pass filter 209 can transmit only a light of a wavelength region which matches a wavelength region of emission of the scintillator in the detector 202.

In the depth dose measuring device according to the second embodiment having the above structure, among lights emitted in the detector 202, only a scintillation light can be incident on the picture measuring device 205 through the band-pass filter 209. Hence, it is possible to accurately measure a depth dose distribution.

Third embodiment

Figure 3:
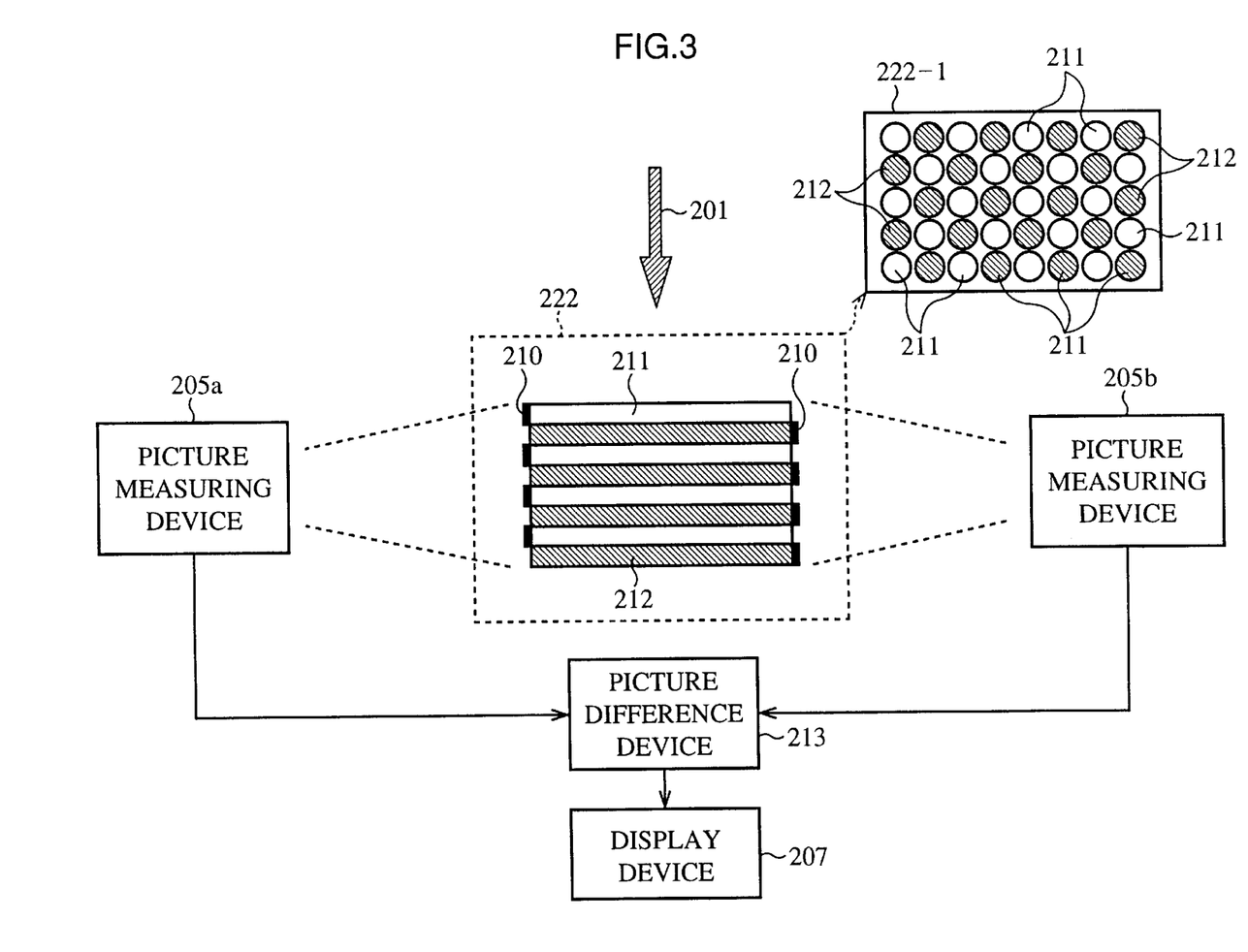
FIG. 3 is a diagram showing a depth dose measuring device according to the third embodiment of the present invention.

FIG. 3 is a block diagram showing a depth dose measuring device according to the third embodiment of the present invention. In the drawing, reference number 222 indicates a detector. The detector 222 comprises a fiber block 222-1 obtained by tying alternating regular optical fibers 211 and scintillation fibers 212 in a bundle. The same reference numbers are used for component parts identical with those in the first embodiment shown in FIG. 1, and descriptions thereof are omitted.

The regular optical fiber 211 is the same as the scintillation fiber 212 in material, but differs from the scintillation fiber 212 simply in that fluorescent material is added to the latter.

A shielding film 210 is provided at an end of the detector 222. The shielding film 210 enables a picture measuring device 205a to measure only a light sent from the scintillation fiber 212. Further, a picture measuring device 205b measures only a light sent from the regular optical fiber 211.

Next, a picture difference device 213 subtracts picture output outputted from the picture measuring devices 205a and 205b. That is, an amount of Cerenkov light is subtracted from an amount of light sent from the scintillation fiber 212. It is thereby possible to measure only an amount of scintillation light. As a result, it is possible to accurately measure a depth dose distribution, and display the obtained depth dose distribution on the display device 207.

Fourth embodiment

Figure 4:
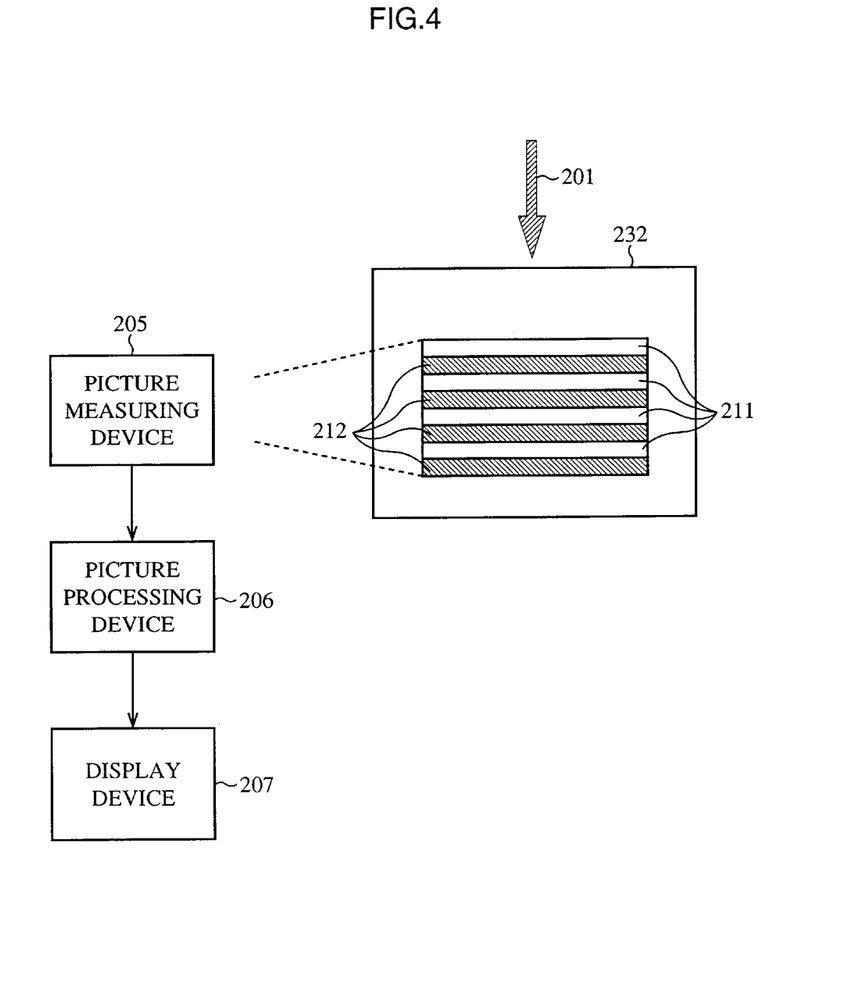
FIG. 4 is a block diagram showing a depth dose measuring device according to the fourth embodiment of the present invention.

FIG. 4 is a block diagram showing a depth dose measuring device according to the fourth embodiment of the present invention. In the drawing, reference number 232 designates a detector. The detector 232 includes a fiber block obtained by tying alternating regular optical fibers 211 and scintillation fibers 212 in a bundle. The same reference numbers are used for component parts identical with those in the first embodiment shown in FIG. 1, and descriptions thereof are omitted.

A picture measuring device 205 measures a light sent from an end surface of the detector 232. As a result, a difference is caused between an amount of light at a position of the scintillation fiber 212 and an amount of light at a position of the regular fiber 211. The difference serves as a difference in display position on picture, and is displayed on a display device 207.

A picture processing device 206 subtracts, from an amount of light at a portion of the scintillation fiber 212, an amount of light at a portion of the regular optical fiber 211 in the vicinity thereof. It is thereby possible to remove an amount of Cerenkov light from the amount of light sent from the scintillation fiber 212. As a result, it is possible to accurately measure a depth dose distribution.

Fifth embodiment

Figure 5:
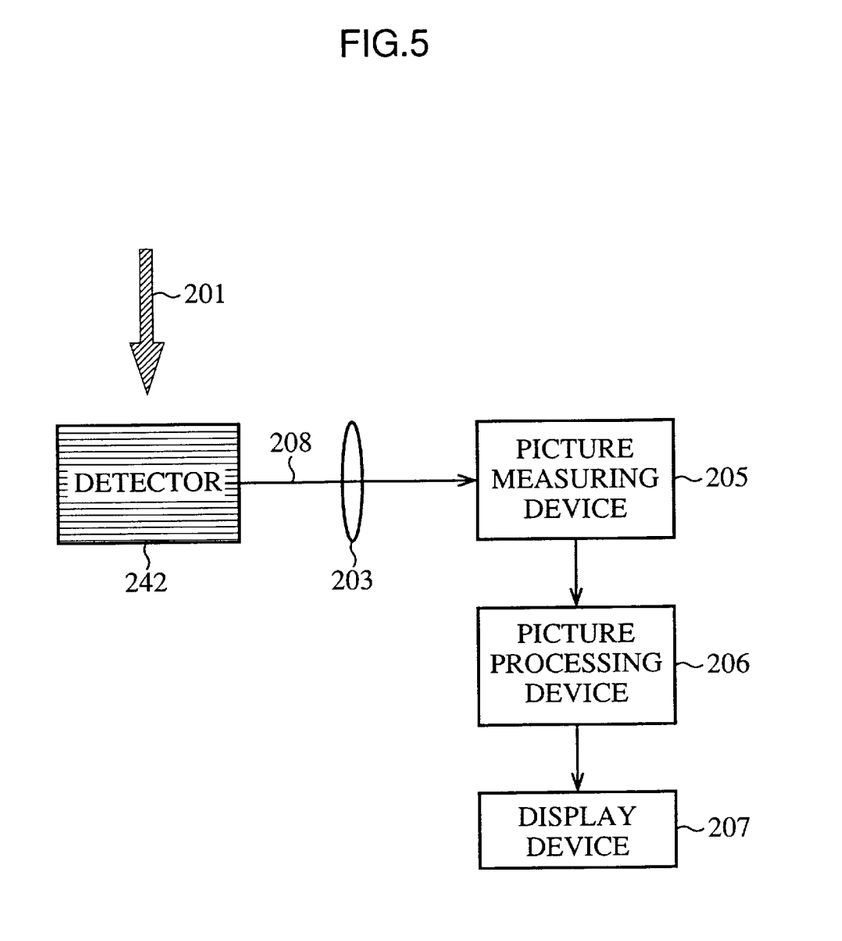
FIG. 5 is a block diagram showing a depth dose measuring device according to the fifth embodiment of the present invention.

FIG. 5 is a block diagram showing a depth dose measuring device according to the fifth embodiment of the present invention. In the drawing, reference number 242 denotes a block-type detector obtained by tying regular optical fibers in a bundle. The same reference numbers are used for component parts identical with those in the first embodiment shown in FIG. 1, and descriptions thereof are omitted.

In the depth dose measuring device according to the fifth embodiment having the structure shown in FIG. 5, the detector 242 comprises a block form obtained by tying the regular optical fibers in a bundle. Hence, the detector 242 can measure only a Cerenkov light, and measures a depth distribution of the Cerenkov light. It is possible to find a depth dose distribution from a distribution of the Cerenkov light depending upon a correlation between a Cerenkov light distribution previously found from the distribution of the Cerenkov light and a depth absorbed dose distribution. It is possible to reduce a cost of a material used for the detector, resulting in an effect of reduction of a cost required to manufacture the depth dose measuring device.

Sixth embodiment

Figure 6:
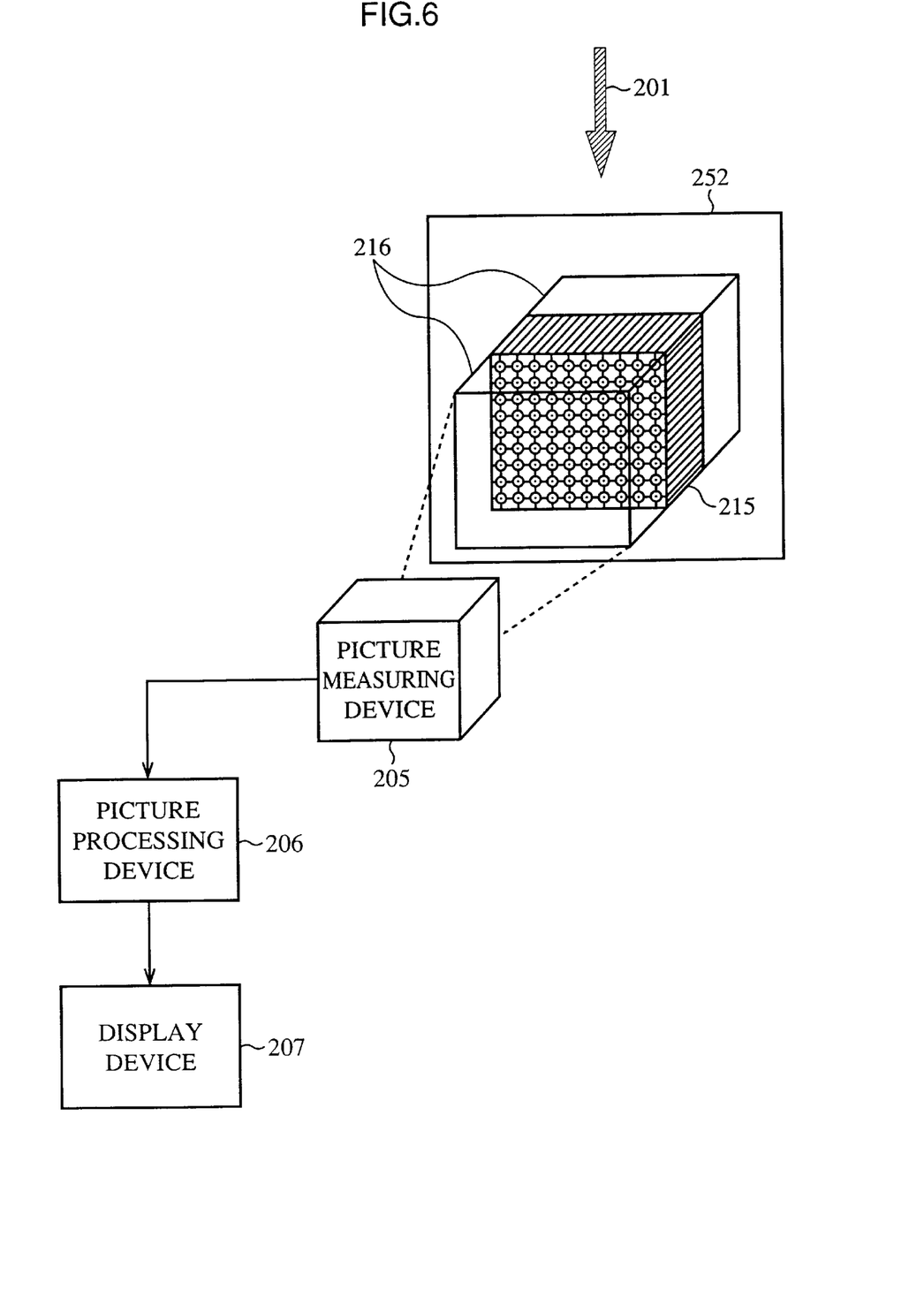
FIG. 6 is a block diagram showing a depth dose measuring device according to the sixth embodiment of the present invention.

FIG. 6 is a block diagram showing a depth dose measuring device according to the sixth embodiment of the present invention. In the drawing, reference number 252 designates a picture measuring device with a detector comprising a short scintillation fiber block 215 and clear plastic blocks 216. The short scintillation fiber block 215 is placed between the clear plastic blocks 216. The same reference numbers are used for component parts identical with those in the first embodiment shown in FIG. 1, and descriptions thereof are omitted.

The clear plastic block 216 is the same as the scintillation fiber block 215 in material, and the detector 252 is homogeneous as a whole. A light is transmitted from an end surface of the scintillation fiber block 215 to the picture measuring device 205 through the clear plastic block 216. The picture measuring device 205 receives and measures the light transmitted from the end surface of the scintillation fiber block 215.

In the depth dose measuring device according to the sixth embodiment, it is possible to enhance the position resolution of absorbed dose, and reduce a material cost for the scintillation fiber block 215 because of the short scintillation fiber block 215 in the detector 252. Even when the scintillation fiber block 215 is short, it is possible to keep an electronic equilibrium state because clear acrylic blocks including the clear plastic blocks 216 are disposed on both sides of the scintillation fiber block 215.

Seventh embodiment

Figure 7:
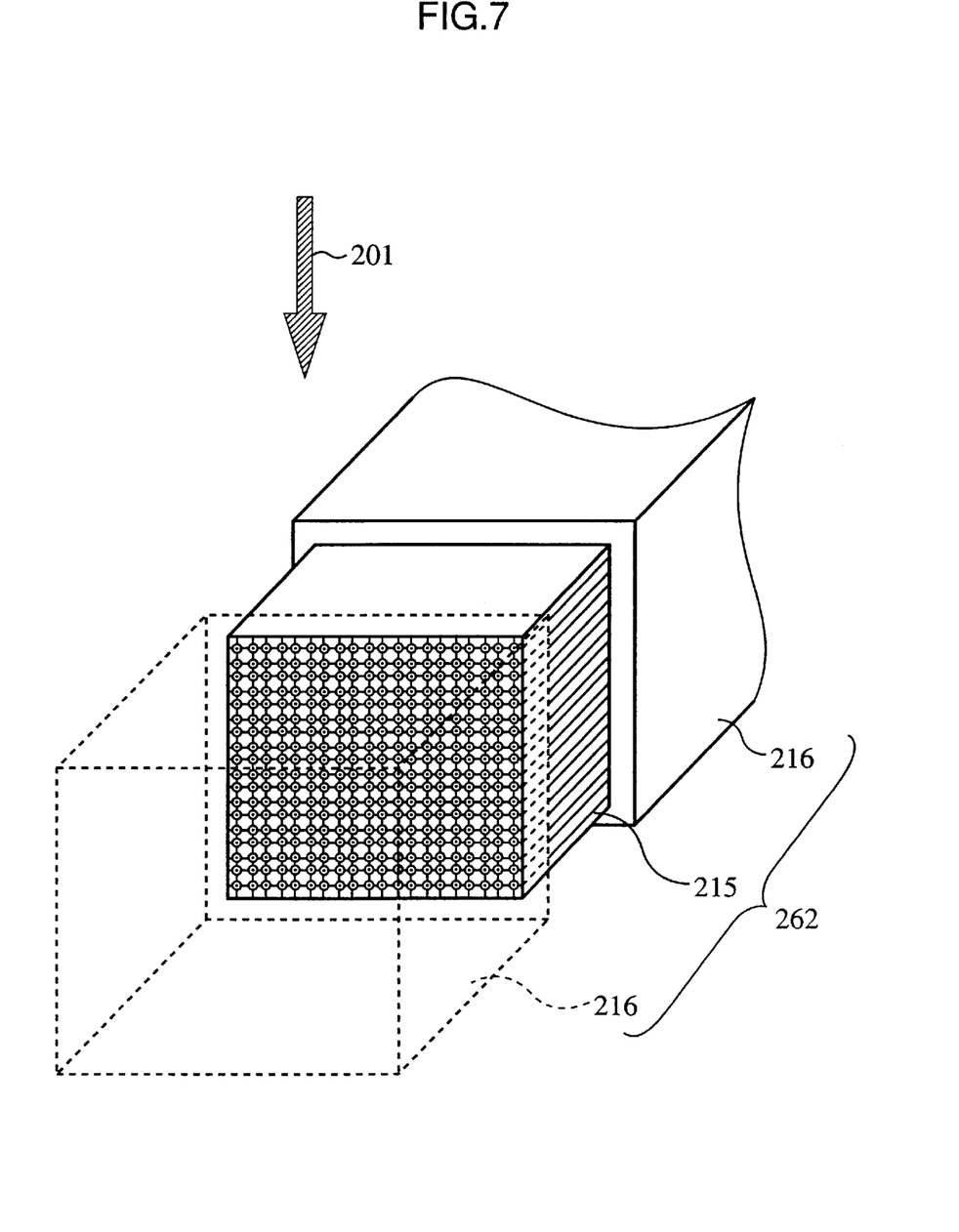
FIG. 7 is a block diagram showing a depth dose measuring device according to the seventh embodiment of the present invention.

FIG. 7 is a block diagram showing a detector in a depth dose measuring device according to the seventh embodiment of the present invention. In the drawing, reference number 262 denotes the detector. Though the detector 262 is enlarged in FIG. 7, component parts of the depth dose measuring device except the detector 262 are identical with those in the fifth embodiment shown in FIG. 6, and descriptions thereof are omitted for the sake of simplicity.

In FIG. 7, reference number 262 designates the detector, 215 is a scintillation fiber block, and 216 is a clear plastic block. The detector 262 comprises the scintillation fiber block 215 and the clear plastic blocks 216.

When the picture measuring device 205 such as a camera is used to measure a light outputted from an end surface of the scintillation fiber block 215, a light outputted from the end surface is partially reflected off side surfaces of the clear plastic block 216. Hence, the clear plastic block 216 is formed to have one side longer than one side of the scintillation fiber block 215 by about 1 cm. It is thereby possible to remove reflection components reflected at the side surfaces of the clear plastic block 216. That is, when the picture measuring device 205 such as a camera is used for shooting, it is possible to remove the reflection components because the side surfaces are disposed apart from a shooting region. As a result, it is possible to measure only a light outputted from the end surface of the scintillation fiber block 215 with high accuracy.

As set forth above, according to the depth dose measuring device of the present invention, the plurality of scintillation fibers are tied in a bundle to provide the block form, and the spectroscope is used to disperse the light outputted from the end surface of the detector so as to measure the amount of light having the wavelength according to the emission spectrum of the scintillation fiber. As a result, it is possible to remove the Cerenkov light, and accurately measure the depth dose distribution at high accuracy.

Further, according to the depth dose measuring device of the present invention, the band-pass filter according to the wavelength of the emission of the scintillation fiber is used to measure the amount of light outputted from the end surface of the detector. As a result, it is possible to remove only the Cerenkov light, and accurately measure the depth dose distribution at high accuracy.

Further, according to the depth dose measuring device of the present invention, the detector comprises the fiber block in which the scintillation fibers and regular optical fibers are alternately disposed. Only the light outputted from the scintillation fiber can be emitted from one end of the detector, and only the light outputted from the regular fiber can be emitted from the other end thereof, resulting in the two measuring systems. Further, a difference is calculated between the signals obtained in both the measuring systems. As a result, it is possible to remove only the Cerenkov light, and accurately measure the depth dose distribution at high accuracy.

Further, according to the depth dose measuring device of the present invention, both the lights outputted from the scintillation fiber and outputted from the regular fiber can be outputted from one end of the detector. The luminance distribution thereof is measured by the picture measuring device such as a camera, and the picture processing is used to calculate the difference between the light outputted from the scintillation fiber and the light outputted from the regular optical fiber. As a result, it is possible to remove only the Cerenkov light, and accurately measure the depth dose distribution at high accuracy.

Further, according to the depth dose measuring device of the present invention, the regular optical fibers are tied in a bundle to form the block-type detector, and the light outputted from the end surface of the detector is measured. Thus, the distribution of the Cerenkov light is measured, and the depth dose distribution is measured by using the correlation between the Cerenkov light distribution and the previously measured depth dose distribution. It is possible to reduce the material cost for the detector, resulting in reduction of the cost required to manufacture the depth dose measuring device.

Further, according to the depth dose measuring device of the present invention, the clear plastic blocks are disposed at both ends of the short scintillation fiber block in the detector. As a result, it is possible to enhance the position resolution of the absorbed dose, and reduce the material cost for the scintillation fiber block.

Further, according to the depth dose measuring device of the present invention, the clear plastic block is formed larger than the scintillation fiber block in size. It is thereby possible to remove only the reflection components at the side surfaces of the clear plastic block. As a result, it is possible to measure the depth dose distribution at high accuracy.

While the above provides a full and complete disclosure of the preferred embodiments of the present invention, various modifications, alternate constructions and equivalents may be employed without departing from the true spirit and scope of the invention. Therefore the above description and illustration should not be construed as limiting the scope of the invention, which is defined by the appended claims.

What is claimed is:

1. A depth dose measuring device comprising:
    detecting means for receiving a particle beam as input, and outputting a scintillation light and a Cerenkov light caused by the particle beam, from an end surface;
    light detecting means for detecting the scintillation light and the Cerenkov light outputted from the detecting means and removing the Cerenkov light, and outputting a detection result;
    picture signal processing means for processing signals from the detection result outputted from the light detecting means; and
    display means for displaying a processing result performed in the picture signal processing means,
    wherein a measurement is made of an amount of the scintillation light having a wavelength corresponding to a light spectrum generated in the detecting means.

2. The depth dose measuring device according to claim 1, wherein the detecting means comprises a block obtained by tying a plurality of scintillation fibers in a bundle, the light detecting means comprising a spectroscope, the light outputted from the detecting means being dispersed by the spectroscope, signals serving as the detection result obtained by the dispersion being inputted into the picture signal processing means, and a measurement being made of an amount of light having a wavelength corresponding to an emission spectrum of the plurality of scintillation fibers.

3. The depth dose measuring device according to claim 1, wherein the detecting means comprises a scintillation fiber block formed by a plurality of scintillation fibers, and clear plastic blocks disposed at both ends of the scintillation fiber block.

4. The depth dose measuring device according to claim 3, wherein the clear plastic blocks are formed to have side surfaces adjacent to said scintillation fiber block which are longer than adjacent side surfaces of the scintillation fiber block.

5. The depth dose measuring device according to claim 1, wherein the detecting means comprises:
    a block obtained by tying a plurality of scintillation fibers in a bundle;
    wherein the light detecting means comprises:
        a band-pass filter corresponding to a wavelength of emission of the plurality of scintillation fibers;
        wherein a light outputted from the end surface of the detecting means passes through the band-pass filter to be inputted into the picture signal processing means; and
        wherein a measurement is made of an amount of light having a wavelength corresponding to an emission spectrum of the plurality of scintillation fibers.

6. A depth dose measuring device comprising:
    detecting means for receiving a particle beam as input, and outputting a light caused by the particle beam from an end surface;
    light detecting means for detecting the light outputted from the detecting means, and outputting a detection result;
    picture signal processing means for processing signals from the detection result outputted from the light detecting means; and
    display means for displaying a processing result performed in the picture signal processing means,
    wherein a measurement is made of an amount of light having a wavelength corresponding to a spectrum of the light generated in the detecting means;
    wherein the detecting means comprises:
        a fiber block formed by alternately disposing a plurality of scintillation fibers and a plurality of regular optical fibers;
        wherein only a light outputted from the plurality of scintillation fibers is outputted from a first end surface of the detecting means;
        wherein only a light outputted from the plurality of regular optical fibers is outputted from a second end surface of the detecting means;
    the picture signal processing means comprising:
        first signal processing means for receiving as input and processing the light outputted from the first end surface;
        second signal processing means for receiving as input and processing the light outputted from the second end surface; and
        the picture signal processing means calculating a difference between a result obtained in the first signal processing means and a result obtained in the second signal processing means.

7. A depth dose measuring device comprising:
    detecting means for receiving a particle beam as input, and outputting a light caused by the particle beam from an end surface;

light detecting means for detecting the light outputted from the detecting means, and outputting a detection result;

picture signal processing means for processing signals from the detection result outputted from the light detecting means; and display means for displaying a processing result performed in the picture signal processing means, wherein a measurement is made of an amount of light having a wavelength corresponding to a spectrum of the light generated in the detecting means;

wherein the detecting means comprises:

a fiber block formed by alternately disposing a plurality of scintillation fibers and a plurality of regular optical fibers;

wherein a first light outputted from the plurality of scintillation fibers and a second light outputted from the plurality of regular optical fibers are outputted from a first end surface of the detecting means;

wherein a luminance distribution of the first light and the second light is measured by picture measuring means;

wherein data of the luminance distribution measured by the picture measuring means is outputted to the picture signal processing means; and wherein the picture signal processing means performs picture processing of input data of the luminance distribution of the first light and the luminance distribution of the second light; and wherein a difference in luminance distribution is calculated between the first light and the second light.

8. A depth dose measuring device comprising:

detecting means for receiving a particle beam as input, and outputting a light caused by the particle beam from an end surface;

light detecting means for detecting the light outputted from the detecting means, and outputting a detection result;

picture signal processing means for processing signals from the detection result outputted from the light detecting means; and display means for displaying a processing result performed in the picture signal processing means, wherein a measurement is made of an amount of light having a wavelength corresponding to a spectrum of the light generated in the detecting means;

wherein the detecting means comprises:

a block formed by tying a plurality of regular optical fibers in a bundle;

wherein a Cerenkov light outputted from an end surface of the detecting means is outputted to the picture signal processing means; and wherein the picture signal processing means obtains a depth dose distribution depending upon a correlation between a distribution of the inputted Cerenkov light and a previously measured depth absorbed dose distribution.

* * * * *